United States Patent
Rialdi

[11] Patent Number: 5,874,410
[45] Date of Patent: Feb. 23, 1999

[54] ARG-GLY-ASP-ASP-SER AND PHARMACEUTICAL COMPOSITIONS AND USES THEREOF

[75] Inventor: Giorgio Rialdi, Genoa, Italy

[73] Assignee: Vevy Europe S.p.A., Genoa, Italy

[21] Appl. No.: 847,354

[22] Filed: Apr. 24, 1997

[30] Foreign Application Priority Data

May 3, 1996 [IT] Italy ................... GE96A0040

[51] Int. Cl.$^6$ .............. A61K 38/08; C07K 7/06
[52] U.S. Cl. ................................ 514/17; 530/330
[58] Field of Search ............... 514/17; 530/330

[56] References Cited

U.S. PATENT DOCUMENTS 4,792,525 12/1988 Ruoslahti et al. ............. 435/240.243

Primary Examiner—Robert J. Hill, Jr.
Assistant Examiner—Anish Gupta
Attorney, Agent, or Firm—Larson & Taylor

[57] ABSTRACT

Pentapeptide having the following formula:

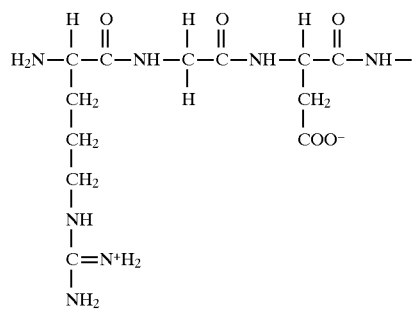

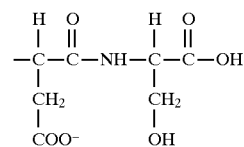

(Arg-Gly-Asp-Asp-Ser).

6 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg  Gly  Asp  Asp  Ser
    1                     5

ARG-GLY-ASP-ASP-SER AND PHARMACEUTICAL COMPOSITIONS AND USES THEREOF

BACKGROUND OF THE INVENTION

The present invention relates to a pentapeptide having the formula

Arg-Gly-Asp-Asp-Ser its pharmaceutical use, as well as a pharmaceutical composition containing the same as active principle.

In general, in the treatment of the skin, and in particular in the treatment of skin lesions, such as wounds, ulcerations or forms of scleroderma, there are known drugs, typically employed for topical application, containing the tetrapeptide Arg-Gly-Asp-Ser. This tetrapeptide is recognized as a fundamental constituent of the glycoprotein fibronectin. Following on extensive research, the protein in question has proved to be of fundamental importance for processes of skin regeneration, both at an epidermal level, and, in particular, at the dermal level. The administration of the tetrapeptide described above makes a significant contribution to the synthesis of fibronectin, and hence helps such processes.

In course of the research that has led to the peptide according to the invention, it has been possible to verify that the introduction of an Asp-Asp pair instead of a single Asp amino acid in the above-mentioned fibronectin-like peptide fragment leads to an increase in activity of the peptide obtained, as compared to the one known, which is not foreseeable on the basis of the data so far available.

SUMMARY OF THE INVENTION

The subject of the invention is therefore a pentapeptide having the following formula:

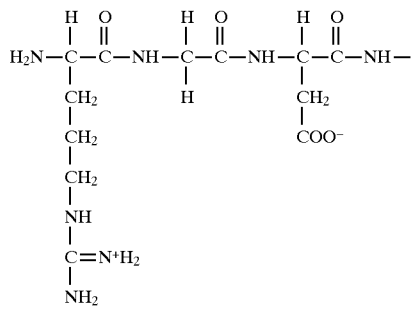

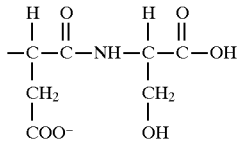

i.e., Arg-Gly-Asp-Asp-Ser (SEQ. ID NO. 1).

A further subject of the invention is a pentapeptide having the above formula for use as a medicament.

Another subject of the invention is the use of the pentapeptide described above for the preparation of a pharmaceutical composition for the treatment of skin lesions, such as wounds, ulcerations or forms of scleroderma.

Another subject of the invention is a pentapeptide of the type described above for use as a cosmetic.

DESCRIPTION OF THE PREFERRED EMBODIMENT

The pentapeptide according to the invention may be synthesized in solid phase, for example with known techniques. The carboxy-terminal amino acid (Ser) is bound to a substrate with a ligand sensitive to trifluoro-acetic acid and with the α-amine group protected, for example, with Fmoc.

After dispersion of the resin in an appropriate solvent (e.g., $CH_2Cl_2$), the group protecting the α-amine group is removed. At this point, the second amino acid (Asp) is activated with the protected amine group. The activation reaction is carried out in anhydrous solvent with DCC and in the presence of 1-hydroxybenzothiazole. Next, the activated amino acid is added to the dispersion of the resin to form the peptide bond. After a certain number of washings, the amine group is de-protected and the operations previously described are repeated for the next three amino acids. At the end of synthesis, an extensive washing of the resin is carried out using the reaction solvent, and then the peptide is removed by means of hydrolysis of the ligand, using trifluoroacetic acid. The peptide is subsequently concentrated in a vacuum and precipitated in diethyl ether to separate it from possible reaction by-products.

The peptide obtained in the manner described above was subjected to a series of tests to evaluate its effectiveness as active principle in dermatopharmacological formulations.

In particular, the starting point was the consideration that the pentapeptide of the invention consists of a short amino acid sequence which can be absorbed percutaneously and which could be deemed capable of stimulating fibronectin synthesis in such a way as to indirectly favour those reactions in the derma that appear to be sustained to a large extent by said protein.

A number of tests were carried out on laboratory animals. The nude mouse was deemed particularly suitable in that, on account of the absence of fur, its skin presents more analogies with human skin than does that of other laboratory animals. Given the evident difficulty in detecting the effects of the pentapeptide of the invention on normal skin, it was judged expedient to cause a lesion artificially and then to assess the reaction of the injured skin to the treatment. In one case, a surgical incision was made, whilst in another case part of the skin was treated with xylol, which is known to damage not only the epidermis, but also the derma, creating a clinical pattern that closely resembles scleroderma.

The present invention is more clearly illustrated by the examples given below.

EXAMPLE 1

Ten female nude mice having a body weight of approximately 20 g were treated for 30 consecutive days, by applying on the skin of the dorsal region, twice daily, with an interval of approximately 10 hours in between, 50 mg of an O/A cream prepared with non-enzymotoxic excipients and containing 5% of an aqueous solution of the pentapeptide of the invention (ratio 1:20). On a further ten mice a control cream devoid of the pentapeptide of the invention was applied. After approximately 14 hours from the last treatment, a 20×3 mm full-thickness strip of skin was removed from each mouse, and the skin was then sutured with three stitches. The process of healing was evaluated by measuring the reduction of the wound in all the mice after four days from removal of the skin. The percentage increase in healing was calculated as follows:

$$\text{Percent increase in healing} = \frac{P - C}{C} \times 100$$

where
P is the mean percentage healing of the mice treated with the cream containing the peptide of the invention
C is the mean percentage healing of the mice treated with the control cream.

The results obtained are given in Table 1.

EXAMPLE 2

The skin of the dorsal region of twenty nude mice of the type described in Example 1 was rubbed with a wad of cotton wool soaked in xylol once a day for approximately one minute, for a total of 5 days. After this treatment, the mice were randomly divided into two lots of 10 mice each. The cream containing the pentapeptide of the invention was applied to one lot of mice, with the same composition and dosage as in Example 1, whereas the control cream was applied on the other lot. The medication was continued until complete healing of the region of skin damaged by the treatment with xylol. The effect of the treatment was assessed by means of the percentage reduction in duration of the therapy until complete recovery, calculated on the basis of the following formula:

$$\text{Percent reduction in therapy} = \frac{mP - mC}{mC} \times 100$$

where
mP is the mean duration (in days) of therapy until complete healing in the cases treated with the cream containing the peptide of the invention
mC is the mean duration (in days) of therapy until complete healing in the cases treated with the control cream
The results obtained are given in Table 2.

TABLE 1

Treatment of a skin wound

| | % healing | |
|---|---|---|
| Mouse No. | (P)* | (C)** |
| 1 | 85 | 60 |
| 2 | 75 | 65 |
| 3 | 80 | 70 |
| 4 | 95 | 75 |
| 5 | 100 | 60 |
| 6 | 70 | 70 |
| 7 | 85 | 80 |
| 8 | 85 | 60 |
| 9 | 80 | 70 |
| 10 | 90 | 65 |
| Mean | 84.5 | 67.5 |

% increase in healing: 25.2%

TABLE 2

Treatment of dermatitis from xylol

| | Healing time (days) | |
|---|---|---|
| Mouse No. | (P)* | (C)** |
| 1 | 12 | 13 |
| 2 | 9 | 15 |
| 3 | 11 | 17 |
| 4 | 8 | 13 |
| 5 | 7 | 14 |
| 6 | 12 | 11 |
| 7 | 10 | 13 |
| 8 | 9 | 16 |
| 9 | 9 | 15 |
| 10 | 11 | 15 |
| Mean | 9.8 | 14.1 |

Reduction in healing time: 30.5%
*treatment with cream containing the pentapeptide
**treatment with control cream The test carrried out in the two examples given above show that the pentapeptide according to the invention exerts a significant dermatotrophic effect, improving the capacity of the skin both to repair a solution of continuity and to recover its normal state of hydration and elasticity after being damaged by a harmful agent. In both cases, as expressed by the data given in Tables 1 and 2 attached, the influence of the presence of the said pentapeptide is tangible and the extent of its effect cannot be estimated.

In addition, assays were carried out on human subjects to verify the dermatotrophic activity of the composition containing the pentapeptide of the invention. In this case, the assessments of the action of the pentapeptide are basically of an aesthetic nature, since it is obviously not possible to repeat the experimental models used in the examples described above on human beings.

EXAMPLE 3

A group of 25 women volunteers, aged between 45 and 55 years, all of whom free from any form of skin disease, underwent self-administered treatment for 60 days with two creams, one of which containing the pentapeptide of the invention, and the other being a control cream. The two creams were supplied in tubes identified with the letters "A" and "B", respectively, without the corresponding contents being specified. The subjects were instructed to apply approximately 3 cm of cream of tube "A" on their right cheek, on the back of their right hand, and on their right knee, and to apply the same amount of cream of tube "B" on the corresponding left parts of the body.

At 30 days from start of treatment and at the end of treatment, the 25 women were separately examined by three dermatologists, who did not know which side of the body had been treated with "A" and which with "B", nor the composition of the said preparations. The assessments were expressed as shown in Table 3.

TABLE 3

Parameters and scores in the assessments of Example 3

| Parameter | Characteristics | Score |
|---|---|---|
| GENERAL APPEARANCE | excellent | 3 |
| | good | 2 |
| | poor | 1 |
| HYDRATION | marked | 3 |
| | average | 2 |
| | poor | 1 |
| WRINKLING | minimal | 3 |
| | average | 2 |
| | marked | 1 |

Table 4 presents the mean results for the areas treated with the cream containing the pentapeptide of the invention and for those treated with the control cream, as well as the index of activity calculated as the ratio between the difference of the two mean assessments and the assessment obtained from the areas treated with the control cream

TABLE 4

| | Mean assessment of effects | | | | Activity index | |
|---|---|---|---|---|---|---|
| | after 30 days | | after 60 days | | 30 | 60 |
| Parameter | (A)* | (B)** | (A)* | (B)** | days | days |
| general appearance | 7.01 | 5.56 | 8.01 | 5.91 | 0.33 | 0.36 |
| hydration | 6.88 | 4.84 | 7.84 | 5.33 | 0.41 | 0.47 |
| elasticity | 6.31 | 5 | 7.29 | 5.58 | 0.26 | 0.31 |
| wrinkling | 6.18 | 4.91 | 6.99 | 5.27 | 0.26 | 0.33 |

*treatment with cream containing the pentapeptide
**treatment with control cream From the data given it may be deduced that in general, already after the first 30 days of treatment, a substantial increase in hydration and elasticity was observed, with an appreciable decrease in the number of smaller wrinkles and in the size of the bigger ones, with a consequent improvement in the overall skin appearance.

From these considerations, it may be stated that the pentapeptide of the invention not only proves effective in treating skin lesions, but also presents a marked dermato-cosmetic activity which is manifested in preserving the basic characteristics of healthy skin that is in good condition, i.e., elasticity, hydration and general appearance.

---

---

I claim:

1. Pentapeptide having the following formula:

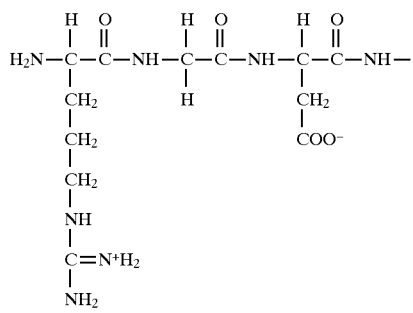

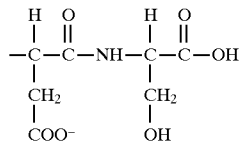

(Arg-Gly-Asp-Asp-Ser (SEQ. ID NO.1)).

2. Pentapeptide (SEQ. ID NO.1) according to claim 1, for use as a medicament.

3. Dermatological pharmaceutical composition comprising the pentapeptide (SEQ. ID NO.1) according to claim 1 as active principle.

4. Pharmaceutical composition comprising from 1 to 10% in weight of a 1:5 to 1:50 (w:w) aqueous solution of the pentapeptide according to claim 1 (SEQ. ID NO.1).

5. Pharmaceutical composition according to claim 5, comprising 5% in weight of a 1:20 (w:w) aqueous solution of the pentapeptide according to claim 1 (SEQ. ID NO.1).

6. A method of treating skin lesions by applying to the skin lesions a pharmaceutical composition comprising the pentapeptide of claim 1 (SEQ ID NO.1) as active principal.

* * * * *